United States Patent [19]
Martens et al.

[11] Patent Number: 4,749,685
[45] Date of Patent: Jun. 7, 1988

[54] IMMUNOSUPPRESSIVE PEPTIDES

[75] Inventors: Christine L. Martens, Menlo Park; Kevin W. Moore, San Bruno, both of Calif.

[73] Assignee: DNAX Research Institute of Molecular and Cellular Biology, Inc., Palo Alto, Calif.

[21] Appl. No.: 892,588

[22] Filed: Aug. 1, 1986

[51] Int. Cl.$^4$ .................. A61K 37/02; C07K 7/10
[52] U.S. Cl. ..................................... 514/12; 530/324
[58] Field of Search ........................... 530/324; 514/12

[56] References Cited

PUBLICATIONS

Akasaki et al., "Immunosuppressive Effects of Glycosylation Inhibiting Factor on the IgE and IgG Antibody Response" *The Journal of Immunology*, vol. 135, pp. 3172-3179 (1986).

Wallner et al., "Cloning and Expression of Human Lipocortin, a Phospholipase A$_2$ Inhibitor with Potential Anti-Inflammatory Activity" *Nature*, vol. 320, pp. 77-81 (1986).

Cloix et al., "Characterization and Partial Purification of 'Renocortins': Two Polypeptides Formed in Renal Cells Causing the Anti-Phospholipase-Like . . . " *Br. J. Pharmac.*, vol. 79, pp. 313-321 (1983).

Hirata et al., "Identification of Several Species of Phospholipase Inhibitory Protein(s) by Radioimmunoassay for Lipomodulin" *Biochem. Biophys. Res. Comm.*, vol. 109, pp. 223-230 (1982).

Ishizaka, K., "Regulation of IgE Synthesis" *Ann. Res. Immunol.*, vol. 2, pp. 159-182 (1984).

Hirata, F. & Iwata, M., "Role of LipoModulin, a Phospholipase Inhibitory Protein, in Immunoregulation by Thymocytes" *The Journal of Immunology*, vol. 130, pp. 1930-1936 (1983).

*Primary Examiner*—John Kight
*Assistant Examiner*—Christina Chan
*Attorney, Agent, or Firm*—Stephen C. Macevicz

[57] ABSTRACT

Immunosuppressive peptides having glycosylation inhibiting factor activity are provided. The peptides include the following sequence and its homologs:

H—Cys—Val—Cys—Val—Cys—Leu—Leu—
Pro—Arg—Tyr—Pro—Ser—Ala—Gly—
Val—Phe—Thr—Tyr—Leu—Asn—Thr—
Lys—Ile—Ile—thr—Phe—Asp—Ser—
Val—Leu—Ser—Lys—Cys—Ala—OH.

14 Claims, No Drawings

IMMUNOSUPPRESSIVE PEPTIDES

BACKGROUND OF THE INVENTION

The present invention relates generally to compounds capable of suppressing immune responses, and more particularly to so-called glycosylation inhibiting factors, which are capable of causing the suppression of immunoglobulin E (IgE) production.

As far as can be determined, the main physiological function of IgE-mediated responses is to combat parasites. The response can be divided into five phases: an IgE-bearing B cell is stimulated to respond to an antigen (phase 1) and activated to secrete IgE antibodies (phase 2); the produced antibodies bind to mast cells and basophils in tissues (phase 3, antibody fixation), interaction of allergen with cell-bound IgE activates these cells, and cause the release of chemical mediators stored in their granules (phase 4, degranulation); and finally, the mediators induce a complex tissue response aimed at the elimination of nonmicrobial parasites from the body (phase 5). Part of this defense mechanism is an attack on the tissue that harbors the parasite—that is, on self. To excise a parasite from a tissue without damaging the rest of the body is an extraordinarily delicate act. The mediators released by activated mast cells and basophils can cause considerable harm, even death, if released at an inappropriate time or if directed at an inappropriate target. The IgE response must be closely controlled and quickly attenuated after its goal has been achieved. As long as this control is functioning there is no danger that healthy parts of the body will be damaged, but should the controls fail, the beneficial reaction will turn into a harmful one. In humans, about 90 percent of all individuals have no difficulty in using their IgE only for defensive purposes; but the remaining unlucky 10 percent carry a genetic defect of the control mechanism that permits the stimulation of IgE responses by antigens that have nothing to do with parasites. At first it was though that this defect was limited only to humans, but similar defects were discovered later in several other mammals. The inappropriately stimulated IgE responses cause a plethora of diverse diseases, grouped under the name allergy or atopy, Klein, *Immunology: The Science of Self-Nonself Discrimination* (John Wiley & Sons, New York, 1982).

Currently glucocorticoid steroids are the most effective drugs for treating allergic diseases. However prolonged steroid treatment is associated with many deleterious side effects, Goodman and Gillman, *The Pharmacological Basis of Therapeutics*, 6th ed. (MacMillan Publishing Company, New York, 1980). Recently, Ishizaka and his co-workers have discovered and characterized a class of compounds which they have designated as glycosylation inhibiting factors (GIFs), Ishizaka, Ann. Rev. Immunol., Vol. 2, pgs. 159-182 (1984). GIFs are natural compounds which are capable of causing T cells to produce a class of IgE binding factors which, in turn, selectively suppress the IgE response (IgE suppressive factors). Apparently, one GIF is related to lipomodulin, a phospholipase inhibitory protein, which is induced by treatment of a variety of cells with glucocorticoid, e.g. Flower et al., Nature, Vol. 278, pgs 456–459 (1979). This GIF inhibits the assembly of N-linked oligosaccharide to IgE binding factors for the selective formation of IgE suppressive factors. It suppresses IgE-induced expression of Fc-epsilon receptors on lymphocytes; the factor has a molecular weight of 15–16 kilodaltons, and it binds to monoclonal antibodies against lipomodulin, Uede et al., J. Immunol., Vol. 130, pgs 878–884 (1983), and Iwata et al, J. Immunol., Vol. 132, pgs. 1286–1294 (1984). Wallner, et al., in Nature, Vol. 320, pgs. 77–81 (1986) report the cloning, sequencing and expression of human lipocortin (lipocortin being another name for lipomodulin).

In view of the foregoing it would be advantageous to develop further immunosuppressive compounds, particularly GIFs, which are effective in reducing or eliminating inappropriate IgE responses, but which do not introduce unwanted side effects.

SUMMARY OF THE INVENTION

The present invention is a group of immunosuppressive peptides whose amino acid sequences are derived from a native nucleotide sequence capable of expressing GIF activity. The immunosuppressive peptides of the invention are defined by the formula:

Formula I

H—Cys—X(Val)—Cys—X(Val)—Cys—X(Leu)—
X(Leu)—X(Pro)—X(Arg)—X(Tyr)—X(Pro)—Ser—
X(Ala)—Gly—X(Val)—X(Phe)—Thr—X(Tyr)—
X(Leu)—X(Asn)—Thr—X(Lys)—X(Ile)—X(Ile)—
Thr—X(Phe)—X(Asp)—Ser—X(Val)—X(Leu)—
Ser—X(Lys)—Cys—X(Ala)—OH wherein the term X (Xaa) represents the group of synonymous amino acids to the amino acid Xaa.

Synonymous amino acids within a group have sufficiently similar physiochemical properties that substitution between members of the group will preserve the biological function of the peptide, Grantham, Science, Vol. 185, pgs 862–864 (1974). It is clear that insertions and deletions of amino acids may also be made in the above defined sequence without altering biological functions, particularly if the insertions or deletions only involve a few amino acids, e.g. less than 2–3, and do not remove or displace amino acids which are critical to a functional conformation, Anfinsen, Science, Vol. 181, pgs 223–230 (1973). Peptides differing from those of Formula I by such minor deletions or insertions come within the purview of the present invention.

· Amino acid nomenclature recommended by the following reference is used throughout: Cohn, *Methods in Enzymology,* Vol. 106, pgs. 3–17 (Academic Press, New York, 1984); and IUPAC-IUB Commission, J. Bio. Chem., Vol., 247, pgs. 977–983 (1972).

Preferably the synonymous amino acid groups are those defined by Table I. More preferably, the synonymous amino acid groups are those defined in Table II; and most preferably the peptide of the invention is defined by the following sequence of amino acids:

Formula II

H—Cys—Val—Cys—Val—Cys—Leu—Leu—Pro—
Arg—Tyr—Pro—Ser—Ala—Gly—Val—Phe—Thr—
Tyr—Leu—Asn—Thr—Lys—Ile—Ile—Thr—Phe—
Asp—Ser—Val—Leu—Ser—Lys—Cys—Ala—OH

The invention includes peptides of Formula I with amino acid substitutions (between an amino acid of Formula II and a synonymous amino acid) at a single position or at multiple positions. The term "N-fold substituted" in reference to the peptides of Formula I is used to describe a subset of peptides wherein the amino acids of Formula II have been substituted by synonymous amino acids at no more than N positions. Thus, for example, the group of 1-fold substituted peptides of Formula I consists of 48 peptides for the preferred groups of synonymous amino acids, and 12 peptides for the more preferred groups of amino acids.

As a further example, consider a 1-fold substituted peptide having the sequence:

Ser—X(Lys)—Cys—X(Ala)

(which are the last four amino acids of Formula I). Preferably X(Lys) is the group consisting of Lys and Arg; and most preferably, it is the group consisting solely of Lys. Likewise, X(Ala) preferably is the group consisting of Ala and Pro; and most preferably, it is the group consisting solely of Ala. The term "1-fold substituted" in reference to the above sequence defines two groups of peptides, one with respect to the preferred groups for X(Lys) and X(Ala), and one with respect to the most preferred groups for X(Lys) and X(Ala). The "1" in the term "1-fold substituted" means that the peptides of the groups differ from the sequence, Ser—Lys—Cys—Ala by no more than 1 amino acid substitution. The following list is the group of 1-fold substituted peptides of the above sequence, with respect to the preferred amino acid groups for X(Lys) and X(Ala):

Ser—Lys—Cys—Ala
Ser—Arg—Cys—Ala
Ser—Lys—Cys—Pro

The sequence Ser—Arg—Cys—Pro is not included because it has 2 substitutions. Since the most preferred groups of amino acids for X(Lys) and X(Ala) each only consist of a single amino acid, the group of 1-fold substituted peptides of the above sequence with respect to the most preferred amino acid group consists solely of the sequence, Ser—Lys—Cys—Ala.

The term "N-fold deleted" in reference to the peptides of Formula I is used to describe a set of peptides having from 1 to N amino acids deleted from the sequence defined by Formula I. Thus, the set of 1-fold deleted peptides of Formula I consists of 34 subgroups of peptides each 33 amino acids in length (33-mers). Each of the subgroups in turn consists of all the 33-mers defined by the preferred, and more preferred synonymous amino acid groups.

As a further example, consider the set of 1-fold deleted peptides of the four amino acid sequence defined above:

Ser—X(Lys)—Cys—X(Ala)

X(Lys) and X(Ala) define the same preferred and most preferred groups as described above. The group of 1-fold deleted peptides consists of the following 3-mer sequences of amino acids:

Ser—X(Lys)—Cys
Ser—X(Lys)—X(Ala)
Ser—Cys—X(Ala)

X(Lys)—Cys—X(Ala).

Following a similar procedure, the group of 2-fold deleted peptides of the sequence Ser—X(Lys)—Cys—X(Ala) consists of the following 2-mer sequences:

Ser—X(Lys)   X(Lys)—Cys
Ser—Cys      X(Lys)—X(Ala)
Ser—X(Ala)   Cys—X(Ala)

together with all the 1-fold deleted peptides. Generally, if a sequence is N amino acids long and is k-fold deleted, then the number of subgroups of peptides having deletions if the sum, $$\sum_{i=1}^{k} \binom{N}{N-i}, \text{ where } \binom{N}{N-i} \text{ is the binomial}$$

coefficient (i.e. it represents the number of groups of N-i-mer sequences that can be selected from an N-mer sequence by i deletions).

TABLE I

Preferred Groups of Synonymous Amino Acids

| Amino Acid | Synonymous Group |
|---|---|
| Arg | Arg, His, Lys |
| Leu | Leu, Ile, Phe, Met |
| Pro | Pro, Ala |
| Ala | Ala, Pro |
| Val | Val, Met, Ile |
| Ile | Ile, Met, Phe, Val, Leu |
| Phe | Phe, Met, Tyr, Ile, Leu |
| Tyr | Tyr, Phe |
| Asn | Asn, Asp |
| Lys | Lys, Arg |
| Asp | Asp, Asn |

TABLE II

More Preferred Groups of Synonymous Amino Acids

| Amino Acid | Synonymous Group |
|---|---|
| Arg | Arg |
| Leu | Leu, Ile, Met |
| Pro | Pro |
| Ala | Ala |
| Val | Val |
| Ile | Ile, Met, Leu |
| Phe | Phe |
| Tyr | Tyr |
| Asn | Asn |
| Lys | Lys |
| Asp | Asp |

The invention also includes pharmaceutical compositions comprising one or more peptides of the invention, or their pharmaceutically acceptable salts, and suitable carrier compounds.

The present invention is directed to problems associated with abnormal and/or allergic immune responses involving the production of IgE. In particular, new low molecular weight GIFs are provided which cause T cells of the immune system to preferentially secrete IgE suppressive factors which, in turn, reduce the intensity of an IgE mediated immune response.

DETAILED DESCRIPTION OF THE INVENTION

Peptides of the invention are synthesized by standard techniques, e.g. Stewart and Young, *Solid Phase Peptide Synthesis*, 2nd Ed. (Pierce Chemical Company, Rockford, IL, 1984). Preferably a commercial automated synthesizer is used, e.g. Vega Biochemicals (Tuscon, AZ) models 296A or B, or Applied Biosystems, Inc. (Foster City, CA) model 430A.

The protected peptide of Formula II was assembled by solid phase synthesis on a cross-linked polystyrene support starting from the carboxyl terminal residue and adding amino acids in a stepwise fashion until the entire 34 residue chain had been formed. The synthesis was performed on a fully automated peptide synthesizer (Applied Biosystems, Inc. model 430A). The following references are guides to the chemistry employed during synthesis: Merrifield, J. Amer. Chem. Soc., Vol. 85, pg. 2149 (1963); Kent et al., pg 185, in *Peptides* 1984, Ragnarsson, Ed. (Almquist and Weksell, Stockholm, 1984); Kent et al., pg. 217 in *Peptide Chemistry* 84, Izumiya, Ed. (Protein Research Foundation, B. H. Osaka, 1985); Merrifield, Science, Vol. 232, pgs. 341–347 (1986); and references cited in this latter reference.

In solid state synthesis it is most important to eliminate synthesis by-products, which are primarily termination, deletion, or modification peptides. Most side reactions can be eliminated or minimized by use of clean, well characterized resins, clean amino acid derivatives, clean solvents, and the selection of proper coupling and cleavage methods and reaction conditions, e.g. Barany and Merrifield, *The Peptides*, Cross and Meienhofer, Eds., Vol. 2, pgs 1–284 (Academic Press, New York, 1979). It is important to monitor coupling reactions to determine that they proceed to completion so that deletion peptides missing one or more residues will be avoided. The quantitative ninhydrin reaction is useful for that purpose, Sarin et al. Anal. Biochem, Vol. 117, pg 147 (1981). N$\alpha$-t-butyloxycarbonyl (t-Boc-)—amino acids were used with appropriate side chain protecting groups stable to the conditions of chain assembly but labile to strong acids. After assembly of the protected peptide chain, the protecting groups were removed and the peptide anchoring bond was cleaved by the use of low then high concentrations of anhydrous hydrogen fluoride in the presence of a thioester scavenger, Tam et al., J. Amer. Chem. Soc., Vol. 105, pg. 6442 (1983).

Side chain protecting groups used were Asp(OBzl), Glu(OBzl), Ser(Bzl), Thr(Bzl), Lys(Cl-Z), Tyr(Br-Z), Arg(N$^G$Tos), Cys(4-MeBzl), and His(ImDNP). (Bzl, benzyl; Tos toluene sulfoxyl; DNP, dinitrophenyl; Im, imidazole; Z, benzyloxycarbonyl. The remaining amino acids had no side chain protecting groups. All the amino acids were obtained from Peninsula Laboratories, except the tBoc-His(ImDNP), which was from Chemical Dynamics and was crystallized from ethanol before use. For each cycle the tBoc N$\alpha$ protected peptide-resin was exposed to 65 percent trifluoroacetic acid (from Eastman Kodak) (distilled before use) in dichloromethane (DCM), (Mallenckrodt): first for 1 minute then for 13 minutes to remove the N$\alpha$-protecting group. The peptide-resin was washed in DCM, neutralized twice with 10 percent diisopropylethylamine (DIEA) (Aldrich) in dimethylformamide (DMF) (Applied Biosystems), for 1 minute each. Neutralization was followed by washing with DMF. Coupling was performed with the preformed symmetric anhydride of the amino acid in DMF for 16 minutes. The preformed symmetric anhydride was prepared on the synthesizer by dissolving 2 mmol of amino acid in 6 ml of DCM and adding 1 mmol of dicyclohexycarbodiimide (Aldrich) in 2 ml of DCM. AFter 5 minutes, the activated amino acid was transferred to a separate vessel and the DCM was evaporated by purging with a continuous stream of nitrogen gas. The DCM was replaced by DMF (6 ml total) at various stages during the purging. After the first coupling, the peptide-resin was washed with DCM, 10 percent DIEA in DCM, and then with DCM. For recoupling, the same amino acid and the activating agent, dicyclohexylcarbodiimide, were transferred sequentially to the reaction vessel. After activation in situ and coupling for 10 minutes, sufficient DMF was added to make a 50 percent DMF-DCM mixture, and the coupling was continued for 15 minutes. Arginine was coupled as a preformed hydroxybenzotriazole (Aldrich) ester in DMF for 60 minutes and then recoupled in the same manner as the other amino acids. Asparagine and glutamine were coupled twice as preformed hydroxybenzotriazole esters in DMF, 40 minutes for each coupling. For all residues, the resin was washed after the second coupling and a sample was automatically taken for monitoring residual uncoupled $\alpha$-amine by quantitative ninhydrin reaction, Sarin et al. (cited above).

Standard assays for GIF activity are used to test the synthetic peptides e.g. Iwata et al., J. Immunol., Vol. 132, pgs. 1286–1293 (1984); Uede at al., J. Immunol., Vol. 130, pgs 878–884 (1983); Akasaki et al., J. Immunol., Vol. 136, pgs. 3172–3179 (1986), and Jardieu et al., J. Immunol., Vol. 133, pgs. 3266–3273 (1984). Accordingly, these references are incorporated by reference.

GIF is assayed (1) by its ability to switch T cells from producing IgE binding factors having potentiating activity (IgE-PF) to producing IgE binding factors having suppressive activity (IgE-SF), or (2) by its ability to inhibit IgE-induced expression of Fc-epsilon receptors on lymphocytes. Below, assays applicable to rodent GIFs are described. Some routine experimentation may be required to develop analogous assays for other mammalian species. It is believed that the biological effects of GIFs are interspecific. For example, rat GIF from 23B6 cells (deposited with the American Type Culture Collection, Rockville, MD, under accession number HB8521) have been shown to switch human T cell hybridoma 166A2 (described by Huff and Ishizaka in Proc. Natl. Acad. Sci., Vol. 81, pg. 1514 [1984]) from the production of IgE-PF to the production of IgE-SF.

One method for assaying the ability of GIF to switch T cells from IgE-PF to IgE-SF production, depends on the observation that the differences between IgE-PF and IgE-SF reside in their respective states of glycosylation, and that these differences can be detected by affinity for certain lectins, Martens et al., Proc. Natl. Acad. Sci., Vol. 82, pgs. 2460–2464 (1985). IgE-PF has affinity for lentil lectin and concanavalin A, whereas IgE-SF fails to bind to either lectin, Yodoi et al., J. Immunol., Vol. 128, pg. 289 (1982). Thus, for example, normal BALB/c spleen cells can be used to assay GIF activity as follows. Samples of normal spleen cells (about $1 \times 10^7$ nucleated cells/ml) are cultured for about 24 hours with 10 micrograms/ml mouse IgE in the presence or absence (controls) of the samples to be tested, and the IgE binding factors formed in the cultures are fractionated on a lentil lectin Sepharose column. When normal BALB/c spleen cells are cultured with IgE alone, IgE binding factors formed by the cells are distributed approximately equally between the effluent and eluate fractions. The majority of IgE binding factors formed in the presence of a GIF should fail to bind to the lentil lectin Sepharose.

IgE binding factors in either the effluent or eluate fractions are measured by their ability to inhibit rosette formation between cells having Fc-epsilon receptors and IgE-coated erythrocytes. Red cells coated with human serum albumin (HSA) are used to indicate the level of nonspecific rosettes. IgE-coated erythrocytes are prepared by the method disclosed in Gonzalez-Molina et al., J. Clin. Invest., vol. 59, pg. 616 (1977), with slight modification disclosed in Yodoi and Ishizaka, J. Immunol., Vol. 122, pg. 2579 (1979). Briefly, ox erythrocytes (Colorado Serum Co., Denver, Colo.), are treated successively with trypsin (Miles Laboratories, Erkhart, Ins.), pyruvic aldehyde (ICN Pharmaceutical Inc., Plainview, N.Y.), and formaldehyde, and the fixed cells are kept in phosphate-buffered saline (PBS), pH7.2. Sensitization of fixed erythrocytes with human IgE, rat IgE, or human serum albumin (HSA, 2×crystallized, Nutritional Biochemicals, Cleveland, Ohio) is carried out in 0.1M acetate buffer, pH 5.0. A 4% suspension of fixed erythrocytes is mixed with an equal volume of a protein solution of an appropriate concentration, and the suspensions are rotated for 2 hr at room temperature. An optimal concentration of each protein for sensitization is determined by preliminary experiments. Preferably, about 0.2 mg/ml of human IgE, 0.25 mg/ml of rat IgE, and 0.25 mg/ml of HSA is employed to sensitize the cells. A 1% suspension of the sensitized cells in PBS is stored at 4° C., and the cells are used for rosette formation within 1 week after coupling.

Mesenteric lymph node (MLN) cells from a rat (e.g. Lewis strain, available from Microbiological Associates) infected with the nematode, Nippostrongylus brasiliensis (Nb) can be the source of Fc-epsilon positive cells for the assay. For example, a rat can be infected with 2800–3000 larvae of Nb via a subcutaneous route as described by Ogilvie, in Nature, Vol. 204, pg. 91 (1964). MLN cells are obtained 2–3 weeks after infection using standard procedures, e.g. Ishizaka, et al., Cell. Immunol., Vol. 22, pg. 248 (1976).

The rosette inhibition assay proceeds as follows. About 20 microliters of suspended MLN cells (about $5 \times 10^6$/ml) are incubated for about 10 minutes at 37° C. with an equal volume of a 1% suspension of fixed erythrocytes coated with IgE (or HSA). The cell suspension is then centrifuged at about $90 \times G$ for 5 minutes, and kept at 0° C. for 90 minutes. Pellets are gently mixed with 0.1% toluidine blue in PBS, and then examined in a hemocytometer. At least 300, and preferably 600–1000, cells are counted for enumerating the percentage of rosette-forming cells (RFCs). A positive RFC is defined as a cell having at least three fixed erythrocytes adherent to its surface. HSA-coated fixed erythrocytes are used to quantify the degree of nonspecific rosette formation.

GIFs can also be assayed by direct tests of the IgE-SF activity of the binding factors produced in its presence. A source of binding factors are T cells primed with an antigen known to preferentially elicit an IgE response, e.g. dinitrophenylated ovalbumin (DNP-OA). (Thus, the IgE-BFs from these sources are presumed to have IgE-PF activity, which in the presence of GIF will be switched to IgE-SF activity). As mentioned below, an alternative source of IgE-PFs are supernatants from Cos 7 cells transfected with the plasmid 23B6p8.3, described in Martens et al. (cited above). The suppressive effects of the binding factors are tested on cells which have been induced to produce IgE. In a rodent system, cultures of DNP-OA primed rat mesenteric lymph node (MLN) cells serve as a source of IgE producing cells. The MLN cells are suspended in Click's medium (Cell Immunol., Vol. 3, pg. 264 [1972]) supplemented with 10 percent normal rat serum, $5 \times 10^{-5}$M mercaptoethanol, 100 U/ml of penicillin, and 100 micrograms/ml streptomycin. $10^6$/ml of the cells and 0.1 microgram/ml DNP-OA are cultured in microtiter plates. The suppressive effect on the IgE producing cells is assayed in the presence of IgE-PF (i.e., the assay measures the ability of the suspected IgE-SF to counteract the effects of a known IgE-PF). A 24 hour culture filtrate of MLN cells obtained from rats on the 14th day of Nippostrongylus brasiliensis infection can be employed as a source of IgE-PF. An alternative source of IgE-PFs are supernatants of Cos 7 cells which have been transfected with the plasmid 23B6p8.3, described in Martens et al. (cited above) and deposited with the ATCC under accession number 39633. Both the sample to be tested for suppressive effect and the culture filtrate containing IgE-PF are added to the DNP-OA primed cells. After 5 days of culturing with DNP-OA, the number of IgE-containing cells and $IgG_2$-containing cells developed in the culture are compared with those developed in control cultures that contained only DNP-OA and IgE-PF. Ig expression is determined by immunofluorescence, e.g. via labeled rabbit or goat anti-rat IgE or $IgG_2$ antibodies.

The peptide of Formula II at concentrations of 1 microgram/ml or 0.1 micrograms/ml was found to be capable of switching lectin affinity of IgE binding factor produced by mouse lymphocytes.

For preparing pharmaceutical compositions containing the peptides described by this invention, such peptides are combined in a mixture with preferably inert, pharmaceutically acceptable carriers. Suitable carriers and processes for their preparation are well known in the art (see, e.g., Remington's Pharmaceutical Sciences and U.S. Pharmacopeia: National Formulary, Mack Publishing Company, Easton, PA [1980], which is incorporated herein by reference). The preferred course of administration is parenteral and can include mechanical delivery systems.

Preferably, the pharmaceutical composition is in unit dosage form. In such form, the preparation is subdivided into unit doses containing appropriate quantities of the active component. The quantity of active compound in a unit dose of preparation may be varied or adjusted from 1 μg to 100 mg, according to the particular application and the potency of the active ingredient. The composition can, if desired, also contain other therapeutic agents.

The dosages may be varied depending upon the requirement of the patient, the severity of the condition being treated, the route of administration, and the particular compound being employed. Determination of the proper dosage for a particular situation is within the skill of the art. The term "effective amount" as used herein in reference to the peptides of the invention means the amount necessary to bring about the desired therapeutic effect. It is understood that this amount varies with the circumstances of application, and that some routine experimentation may be required to determine its precise value in particular applications. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The description of the foregoing embodiment of the inventin has been presented for the purpose of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. An immunosuppressive peptide defined by the formula:

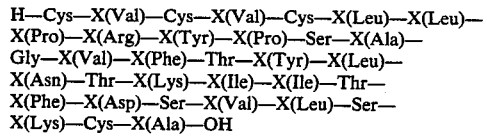

wherein:
X(Arg) represents the group consisting of Arg, His, and Lys;
X(Leu) represents the group consisting of Leu, Ile, Phe, and Met;
X(Pro) represents the group consisting of Pro and Ala;
X(Ala) represents the group consisting of Ala and Pro;
X(Val) represents the group consisting of Val, Met, and Ile;
X(IIe) represents the group consisting of Ile, Met, Phe, Val, Leu;
X(Phe) represents the group consisting of Phe, Met, Tyr, Ile, and Leu;
X(Tyr) represents the group consisting of Tyr and Phe;
X(Asn) represents the group consisting of Asn and Asp;
X(Lys) represents the group consisting of Lys and Arg; and
X(Asp) represents the group consisting of Asp and Asn.

2. The compound of claim 1 wherein:
X(Leu) represents the group consisting of Leu, Ile, and Met;
X(IIe) represents the group consisting of Ile, Met, and Leu;
X(Arg) is Arg;
X(Pro) is Pro;
X(Ala) is Ala;
X(Val) is Val;
X(Phe) is Phe;
X(Tyr) is Tyr;
X(Asn) is Asn;
X(Lys) is Lys; and
X(Asp) is Asp.

3. The compound of claim 2 wherein X(Leu) is Leu and X(IIe) is Ile.

4. The compound of claim 1 consisting of the group of all 2-fold substituted peptides of the formula:

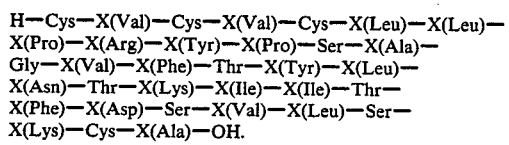

5. The compound of claim 4 consisting of the group of all 1-fold substituted peptides of the formula:

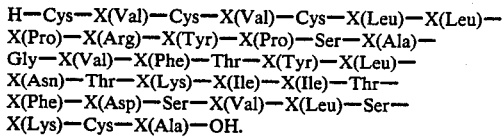

6. An immunosuppressive peptides selected from the group consisting of all 2-fold deleted peptides of the formula:

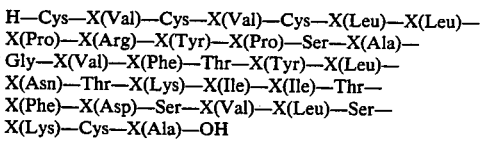

wherein:
X(Arg) represents the group consisting of Arg, His, and Lys;
X(Leu) represents the group consisting of Leu, Ile, Phe, and Met;
X(Pro) represents the group consisting of Pro and Ala;
X(Ala) represents the group consisting of Ala and Pro;
X(Val) represents the group consisting of Val, Met, and Ile;
X(IIe) represents the group consisting of Ile, Met, Phe, Val, Leu;
X(Phe) represents the group consisting of Phe, Met, Tyr, Ile, and Leu;
X(Tyr) represents the group consisting of Tyr and Phe;
X(Asn) represents the group consisting of Asn and Asp;
X(Lys) represents the group consisting of Lys and Arg; and
X(Asp) represents the group consisting of Asp and Asn.

7. The immunosuppressive peptide of claim 6 wherein:
X(Leu) represents the group consisting of Leu, Ile, and Met;
X(Iie) represents the group consisting of Ile, Met, and Leu;
X(Arg) is Arg;
X(Pro) is Pro;
X(Ala) is Ala;
X(Val) is Val;
X(Phe) is Phe;
X(Tyr) is Tyr;
X(Asn) is Asn;
X(Lys) is Lys; and
X(Asp) is Asp.

8. The immunosuppressive peptide of claim 7 selected from the group consisting of all 2-fold deleted peptides of the formula:

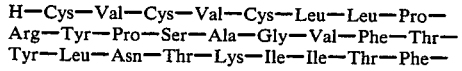

-continued
Asp—Ser—Val—Leu—Ser—Lys—Cys—Ala—OH.

9. The immunosuppressive peptide of claim 6 selected from the group consisting of all 1-fold deleted peptides of the formula:

H—Cys—X(Val)—Cys—X(Val)—Cys—X(Leu)—X(Leu)—
X(Pro)—X(Arg)—X(Tyr)—X(Pro)—Ser—X(Ala)—
Gly—X(Val)—X(Phe)—Thr—X(Tyr)—X(Leu)—
X(Asn)—Thr—X(Lys)—X(Ile)—X(Ile)—Thr—
X(Phe)—X(Asp)—Ser—X(Val)—X(Leu)—Ser—
X(Lys)—Cys—X(Ala)—OH.

10. The immunosuppressive peptide of claim 9 wherein:
X(Leu) represents the group consisting of Leu, Ile, and Met;
X(Ile) represents the group consisting of Ile, Met, and Leu;
X(Arg) is Arg;
X(Pro) is Pro;
X(Ala) is Ala;
X(Val) is Val;
X(Phe) is Phe;
X(Tyr) is Tyr;
X(Asn) is Asn;
X(Lys) is Lys; and
X(Asp) is Asp.

11. The immunosuppressive peptide of claim 10 selected from the group consisting of all 1-fold deleted peptides of the formula:

H—Cys—Val—Cys—Val—Cys—Leu—Leu—
Pro—Arg—Tyr—Pro—Ser—Ala—Gly—Val—
Phe—The—Tyr—Leu—Asn—Thr—Lys—Ile—
Ile—Thr—Phe—Asp—Ser—Val—Leu—Ser—
Lys—Cys—Ala—OH

12. A pharmaceutical composition for suppressing the IgE immune response comprising a therapeutically compatible carrier and an effective amount of a peptide of claim 1, or 6.

13. The pharmaceutical composition of claim 12 wherein said peptide is selected from the group of peptides defined by claim 4, or 9.

14. The pharmaceutical composition of claim 13 wherein said peptide is selected from the group of peptides defined by claim 3, or 11.

* * * * *